United States Patent [19]

Liberti et al.

[11] Patent Number: 5,512,332

[45] Date of Patent: Apr. 30, 1996

[54] PROCESS OF MAKING RESUSPENDABLE COATED MAGNETIC PARTICLES

[75] Inventors: Paul A. Liberti, Hungingdon Valley; Steven P. Piccoli, Morrisville, both of Pa.

[73] Assignee: Immunivest Corporation, Wilmington, Del.

[21] Appl. No.: 231,379

[22] Filed: Apr. 22, 1994

Related U.S. Application Data

[63] Continuation-in-part of Ser. No. 397,106, Aug. 22, 1989, which is a continuation-in-part of Ser. No. 245,351, Sep. 16, 1988, Pat. No. 5,449,404, which is a continuation of Ser. No. 906,521, Sep. 16, 1986, Pat. No. 4,795,698, which is a continuation-in-part of Ser. No. 784,863, Oct. 4, 1985, abandoned.

[51] Int. Cl.$^6$ ........................................................ H01F 1/00
[52] U.S. Cl. .................... 427/550; 427/127; 427/215; 427/299; 427/333; 427/340; 427/407.1; 427/414; 427/443.2; 427/560; 427/598; 427/601
[58] Field of Search ................................. 427/127, 560, 427/601, 550, 598, 215, 299, 333, 340, 407.1, 414, 443.2

[56] References Cited

U.S. PATENT DOCUMENTS

| | | | |
|---|---|---|---|
| 3,215,572 | 10/1963 | Papell | 149/2 |
| 3,970,518 | 7/1976 | Giaever | 195/1.5 |
| 4,018,886 | 4/1977 | Giaever | 424/12 |
| 4,070,246 | 1/1978 | Kennedy et al. | 195/99 |
| 4,152,210 | 5/1979 | Robinson et al. | 195/63 |
| 4,230,685 | 10/1980 | Senyei et al. | 424/12 |
| 4,329,241 | 5/1982 | Massart | 252/62.52 |
| 4,335,094 | 6/1982 | Mosbach | 424/1 |
| 4,452,773 | 6/1984 | Molday | 424/1.1 |
| 4,454,234 | 6/1984 | Czerlinski | 436/526 |
| 4,554,088 | 11/1985 | Whitehead et al. | 252/62.54 |
| 4,672,040 | 6/1987 | Josephson | 436/526 |
| 4,775,636 | 10/1988 | Moeremans et al. | 436/518 |
| 4,795,698 | 1/1989 | Owen et al. | 435/4 |

FOREIGN PATENT DOCUMENTS

| | | |
|---|---|---|
| 0230768 | 12/1985 | European Pat. Off. . |
| 0391608 | 4/1989 | European Pat. Off. . |

OTHER PUBLICATIONS

J. G. Atherton and S. S. Bell, Water Res., 17:943–948 (1983) no month avail.

J. G. Atherton and S. S. Bell, Water Res., 17: 949–953 (1983) no month avail.

Jane A. Langdale and Alan D. B. Malcolm, Biochemical Society Transactions 12: 693–694 (1984) (no month avail.).

M. Nakagaki and M. Tagawa, Yakugaku Zasshi, 99: 65–70 (1979) [Abstract in English] (no month avail.).

Renshaw et al., Magnetic Resonance Imaging, 4: 351–357 (1986 (no month avail.).

Kandori et al., Nippon Kagaku Kaishi, 9: 1357–1361 (1984) [Abstract in English ] (no month avail.).

*Primary Examiner*—Bernard Pianalto
*Attorney, Agent, or Firm*—Dann, Dorfman, Herrell and Skillman

[57] ABSTRACT

A method is provided for direct coating of transiently stable, colloidal particulate magnetic substrates with various synthetic or naturally-occurring polymers, particularly biologically-active peptides and proteins. The resulting coated resuspendable, colloidal magnetic particles are particularly adapted for use in bioanalytical procedures involving affinity separation, or the like. There is also provided a method for selectively binding chemically-treated colloidal magnetic particles to polyelectrolytes, e.g., to facilitate extraction of nucleic acids from cell lysates.

22 Claims, No Drawings

PROCESS OF MAKING RESUSPENDABLE COATED MAGNETIC PARTICLES

This application is a continuation-in-part of pending U.S. patent application Ser. No. 397,106, filed Aug. 22, 1989, which is a continuation-in-part of pending U.S. patent application Ser. No. 245,351, filed Sep. 16, 1988, now U.S. Pat. No. 5,449,404, which is a continuation of application Ser. No. 906,521, filed Sep. 16, 1986, now U.S. Pat. No. 4,795,698, which is a continuation-in-part of application Ser. No. 784,863, filed Oct. 4, 1985, now abandoned. The disclosure of the aforementioned related applications are incorporated herein by reference.

FIELD OF THE INVENTION

This invention pertains to stable suspensions of magnetic particles and to resuspendable coated magnetic particles, preferably, but not limited to, those having biochemical or biological activity, to compositions including such particles, and to methods of making and using such particles and compositions.

Biologically active magnetic particles find use in a variety of preparative and diagnostic techniques. Among these is high gradient magnetic separation (HGMS) which uses a magnetic field to separate magnetic particles from suspension. In instances where these particles are attached to biological materials of interest (e.g., cells, drugs), the material of interest or target material may thereby be separated from other materials not bound to the magnetic particles. Because of their magnetic properties, these materials also function as contrast agents for magnetic resonance imaging.

As used herein, the term "resuspendable coated particle" refers to a finely divided solid, which forms a colloidal suspension and may be separated from the suspension and subsequently resuspended. "Magnetic" encompasses material which may or may not be permanently magnetic, which also may be paramagnetic or superparamagnetic but which in all cases exhibits a response in a magnetic field, i.e., is magnetically responsive. "Disrupted" particles are those which are too small to contain a complete magnetic domain or, alternatively, whose Brownian energy exceeds their magnetic moment. Generally, these particles are less than $0.03\mu$ in size.

DESCRIPTION OF RELATED ART

Many techniques have been suggested in the prior art for the preparation of magnetic particles or organo-magnetic materials. Such particles generally fall into three categories: large, small and microagglomerates of small particles. Large magnetic particles, having diameters greater than $10\mu$ respond to weak magnetic fields and magnetic field gradients. Because of their size, they tend to settle rapidly from solution and also have limited surface area per unit weight. Large particles also tend to aggregate after they have been subjected to a magnetic field because they can be permanently magnetized. Small particles which have magnetic cores of mean diameter less than $0.03\mu$ remain in solution by virtue of their Brownian energy and hence do not spontaneously settle. Microagglomerates of such small magnetic particles have been prepared by various methods. Depending on the size of the microagglomerates, materials which can remain in solution for reasonable periods of time can be prepared. Additionally, the magnetic properties of small particles and microagglomerates of small magnetic particles are significantly different from those of the larger permanently magnetizable particles. Small magnetic particles composed of either single crystals of ferromagnetic materials such as iron oxides or agglomerates of such crystals become "super-paramagnetic" when the crystal size of the ferromagnetic materials is below about 300 Å. Unlike ferromagnetic crystals, superparamagnetic crystals only exhibit magnetic behavior when they are in a magnetic field gradient and do not become permanently magnetized. Such materials have been referred to as dispersible magnetic metal oxide particles and also as magnetically responsive particles.

One possible route to obtaining a magnetic particle bearing a bioreceptor is that of U.S. Pat. Nos. 3,970,518 and 4,018,886 to Giaever, which teach the physical coating of such materials onto the magnetic particles via adsorption. The coating of bovine serum albumin onto $1\mu$ diameter nickel particles is exemplified.

U.S. Pat. No. 4,230,685 to Senyei et al. considers the teaching of U.S. Pat. No. 3,970,518 and states that there is "no literature verification that uncoated magnetic particles can effectively be made to bind with antibody" and presumably other bioreceptors. U.S. Pat. No. 4,554,088 to Whitehead et al. states that antibodies adsorbed on iron oxides are substantially detached by 24-hour 50° incubation in 1 M sodium chloride and also that the quantity of adsorbed material is low.

With respect to one type of superparamagnetic particle described herein, namely, colloidal particles, the method of recovery proposed in U.S. Pat. Nos. 3,970,518 and 4,018,886 could not easily be made to work on such colloidal particles, as the field strength required to capture such particles for washing away unadsorbed materials would be enormous. Additionally, a field gradient is required, which is not achievable with the apparatus there described. In conjunction with the preparative use of high gradient magnetic separation (HGMS), the concept of Giaever might work where there are effective means for adsorbing and retaining antibodies or bioreceptors on such particles.

In view of the apparent failure to produce functionally acceptable magnetic particles via bioreceptor adsorption, a number of ingenious innovations have been reported. These include U.S. Pat. No. 4,230,685 to Senyei et al., which discloses the preparation of microspheres containing magnetite, albumin, and protein A. The preparation taught by Senyei involves an emulsion polymerization of the above ingredients. U.S. Pat. No. 4,554,088 to Whitehead et al. teaches the silanation of magnetic metal oxides which subsequently can be covalently linked to bioactive molecules. Both of the preceding teachings deal with agglomerated superparamagnetic particles; hence, the agglomerated materials are classed as magnetically responsive. Other patents which may be considered to be of interest include U.S. Pat. Nos. 4,152,210 to Robinson et al.; 4,335,094 to Mosbach; 4,070,246 to Kennedy et al.; and 4,454,234 to Czerlinski. While these patents disclose the preparation or use of magnetic-biologic particles, none of these are considered to be similar to those of the present invention.

U.S. Pat. No. 4,452,773 to Molday discloses "colloidal" iron oxide particles coated with non-ionic polysaccharide by forming magnetite in 25% (w/w) polysaccharide solutions. Molday further teaches the covalent linking of bioactive molecules to such formed particles by well-known chemical linking technology. U.S. Pat. No. 4,795,698 to Owen et al., which is incorporated by reference herein, teaches the preparation of colloidal sized metal oxide particles which are coated in what is believed to be a covalent manner by polymers or proteins which have substantial numbers of unpaired electrons. Bioactive molecules such as antibodies or enzymes retain biological activity in the Owen et al. process which involves (1) the coprecipitation of transition element oxides and polymer or protein at 0.1 to 1 mg/ml by titration with base to slightly alkaline pH, (2) the subsequent washing of the coprecipitate and (3) the resuspension of the coprecipitate in appropriate buffers followed by mild sonication resulting in colloidal magnetically responsive particles. In that process, nearly all of the polymer or protein is precipitated. When the preparation of dextran-coated particles was attempted according to the process conditions of Owen et al., a resuspendable colloidal particle could not be obtained. That result, along with the fact that Owen et al. requires coprecipitation with polymers having substantial numbers of unpaired electrons (in contrast to dextran and the other nonreactive polysaccharides which Molday teaches) which apparently interact directly with transition metals, indicates that the processes of Molday and Owen et al. are substantially different. It should also be noted that the Owen et al. process requires the protein or polymer to be in water or low ionic strength buffer.

In view of the apparent absence of interaction of ferric and ferrous ions with dextran and the nature of the Molday dextran particle, it is instructive to examine the process taught therein. The colloidal particles of Molday are prepared by forming magnetite from ferric and ferrous chlorides with $NH_4OH$ in the presence of 25% (w/w) aqueous Dextran T-20 (Pharmacia) or other similarly concentrated polysaccharides. Aggregates formed in the process are subsequently removed by three cycles of centrifugation at low G force. Colloidal dextran magnetite in the supernatant is recovered following gel filtration which separates the unreacted dextran from the colloidal particle which appears in the void volume. A substantial quantity of free dextran exists after the particles are formed. Although there is no discussion of the mechanism for colloidal dextran formation, it seems reasonable to suggest that dextran plays a physical or "barrier" role in the process. The basis for this suggestion is that 25% (w/w) dextran solutions are extremely viscous with extensive hydrogen bonding due to the interaction of its abundant hydroxyl groups with water. These factors create a system which limits diffusion. This would enable ferric and ferrous ions interacting with base to form local crystal nucleation sites whose growth will be related to the ability of bystander ions to participate. The presence of dextran could thus limit ionic participation resulting in the formation of small magnetite crystals (less than 300 Å) which then are capable of adsorbing dextran molecules onto their surfaces. Thus, in this scenario, the dextran plays several roles in the process.

An alternative mechanism for formation of the Molday dextran magnetite is related to a fundamental property of magnetite. From the electron micrographs of Whitehead et al. and from the descriptive material of Senyei et al., it appears that magnetite prepared by the usual base precipitation of iron chlorides is composed of stable crystal of about 300 Å or less in size. In view of the absence in the literature of reports indicating that magnetite can be made into a stable colloidal dispersion, it would seem that these crystals have a strong tendency to aggregate via mutually attractive molecular forces. On the other hand, by forming crystals "in situ" and in "chambers" formed by the high concentration of dextran employed by Molday and by having the "walls" of these individual chambers being able to collapse onto and coat such crystals, Molday appears to have been able to achieve the production of a colloidally stable magnetic particle. In view of the immense difference in surface areas provided by such individual magnetite crystals in contrast to the materials of Giaever, Molday appears to have additionally serendipitously solved the adsorption problem for certain polysaccharides.

U.S. Pat. No. 4,452,773 to Molday discloses a method for making colloidal iron oxide particles coated with non-ionic polysaccharides by forming magnetite in 25% (w/w) polysaccharide solutions. Molday further teaches the covalent linking of bioactive molecules to particles thus formed.

U.S. Pat. No. 4,795,698 to Owen et al. teaches the preparation of colloidal sized resuspendable bioactive magnetic particles by the coprecipitation of transition element oxides and either (a) a bioactive compound, such as a polymer or protein, or (b) a ligand for bioactive compounds.

The significance of the size of bioactive, magnetically responsive particles, for NMR (or MRI) imaging, is disclosed, for example, in Renshaw, Owen, Evans and Leigh, in Magnetic Resonance Imaging 351 (1986).

A colloidal dispersion of magnetic particles in rocket fuel is disclosed in U.S. Pat. No. 3,215,572 to Papell. The dispersion is said to include magnetic particles, such as magnetite ($Fe_3O_4$), 0.25μ in diameter and smaller, preferably less than 0.10μ in diameter. The dispersion is produced by ball milling a suspension of larger particle size magnetic particles in the propellant, with a grinding agent, which prevents "agglomeration or welding of the minute particles as grinding progresses." (column 2, lines 33–34). The ball mill includes metal balls to produce the grinding action. The grinding agent, generally included at levels on the order of 2% but possibly 10%, typically comprises oleic acid; further " . . . other grinding agents such as stearic acid and cetyl alcohol may be utilized in the production of a magnetic propellant and other long chain hydrocarbons having similar high surface tensions, such as benzene, ethane, hydrazine and gasoline may be utilized as the particle carrier and major constituent of the magnetic propellant," (column 4, lines 5–6).

SUMMARY OF THE INVENTION

This invention relates in part to new methods for simplified production of magnetically responsive superparamagnetic particles. According to one aspect of the invention, a process is provided whereby magnetically responsive metal oxides can be coated effectively by employing in the coating process means for disrupting crystalline agglomerates such that coating can take place while the resultant crystals are in the disrupted state. A wide range of materials (including dextran, proteins, synthetic polypeptides, polymers, copolymers, detergents and combinations thereof) can be coated onto such crystals resulting in colloidal magnetically responsive particles. In addition to obtaining a colloidal product, it is possible in most instances, by limiting the amount of coating material, to obtain stable microagglomerates which retain adsorbed material in an extremely effective fashion and which can be removed from solution with simple laboratory magnets.

Magnetic particles of small size (maximum particle size generally below 0.2μ) with a stabilizing (preferably biochemically or biologically active) coating, are produced, in accordance with one embodiment of the process of the invention, by forming a suspension of somewhat larger size parent magnetic particles (believed to be agglomerates), together with a material adapted to form a coating on the relatively smaller, subdivided "sub-particles" upon subdivision of the parent particles. This mixture is then treated to subdivide or disrupt the parent particles and to maintain those particles in that state while simultaneously permitting the coating material to form a coating on the deagglomerated or subdivided particles, thus stabilizing them at reduced particle size. The product is a stable suspension.

With the proper selection of coating material, the coated, subdivided particle product can be separated and resuspended. The resultant resuspendable product, if the stabilizing coating is a bioactive compound or ligand, is particularly useful as an MRI contrast agent, for bioanalytical applications and for industrial bioprocessing.

The magnetic particles of the invention can also be prepared by an alternative direct coating process performed on a transiently stable particulate magnetic substrate, which is further described hereinbelow. In carrying out this embodiment of the invention, a particulate magnetic starting material is divided into a plurality of aggregable, smaller sized particles, thereby providing a bare or uncoated particulate magnetic substrate. The particulate magnetic substrate thus obtained, suspend in a suitable liquid medium, is then contacted with an appropriate coating material, before substantial particulate magnetic substrate aggregation occurs, for a time sufficient for the coating material to adhere to the substrate particles, thereby yielding the desired resuspendable, coated magnetic particles.

Thus, it is not essential to subdivide the particulate magnetic starting material in the presence of the coating material in order to obtain useful colloidal magnetic particles coated with a biologically active biofunctional ligand, for example. Rather, this latter embodiment enables the coating of pre-formed, transiently stable particulate magnetic substrate. The period of stability of the substrate particles is readily determinable by routine experiment in the manner described below. This approach provides certain notable advantages, among which is avoidance of any deleterious effects that the selected disruption technique may have on the coating material. Moreover, sequential addition of coating materials eliminates certain operational restrictions inherent in the embodiment in which the particulate starting material is subdivided in the presence of the coating material. This may be of some importance where the primary coating material is present in a mixture with other substances having greater affinity for the magnetic particulate substrate. Also, because sequential coating affords greater control of the amount of coating material used, work up of the final product is greatly simplified.

The application of additional coating materials, e.g., a particle dispersion aid, to the particles bearing the primary coating material is also contemplated to be within the scope of this invention.

Also in accordance with the present invention, there is provided a method for selective binding of various polyelectrolytes, e.g., DNA or RNA, to the resuspendable, colloidal magnetic particles described herein, which may be used to advantage in performing an array of bioanalytical techniques, such as polymerase chain reaction (PCR) or nucleic acid sequencing. This method comprises providing chemically-treated, resuspendable, colloidal particulates, which have a surface charge that is opposite in polarity to charge on the polyelectrolyte, the surface charge on the chemically-treated, resuspendable, colloidal particulates being the same as or different from any existing charge on the colloidal particulates prior to chemical treatment, and contacting a sample comprising the polyelectrolyte with the chemically-treated, resuspendable colloidal particulates, whereby the colloidal particulates directly bind to the polyelectrolyte, thereby forming an agglomerated mass consisting essentially of the polyelectrolyte and the particulates.

Once the polyelectrolyte is captured on the chemically-treated, resuspendable magnetic particles, it is readily removed from the test sample by magnetic separation, using, for example, the apparatus and methods of U.S. Pat. No. 5,186,827 or U.S. Pat. No. 5,200,084, which are commonly assigned with the present application. The entire disclosures of both of the last-mentioned patents are incorporated by reference in the present specification as if set forth herein in full. Also substantially pure polyelectrolyte can be recovered by appropriate manipulation of ionic strength or pH. A suitable recovery procedure is exemplified below. In this way, extraction of nucleic acids from complex mixtures, such as cell lysates, can be facilitated.

The chemically-treated, resuspendable colloidal magnetic particles used in performing the above-described method for selective binding of polyelectrolytes are considered to be unique in that target recognition and separation capabilities are combined in the individual treated particles. That is to say, affinity between the polyelectrolyte and the chemically-treated surface of the colloidal magnetic particles is essentially due to physical interaction. No additional affinity reagents or procedures for their application to the magnetic particles is required. Further, the small size of the magnetic particles provides increased reaction kinetics, and allows many particles to be bound to the target molecule, enhancing the magnetic responsiveness of the target molecule.

Preferably, the means for disrupting the parent magnetic particle starting material in the suspension is sonication, but other mechanical or chemical means may also be used. These other "means" include, for example, heating, other forms of particle energization, such as irradiation, and chemical means, such as pH modification or combinations of these types of treatment. In particular, a combination of pH modification and sonication may also be used.

According to another aspect of this invention, there is provided an acid-treated, resuspendable, colloidal particles, having a maximum particle size below 0.2 microns, which bind directly to negatively charged polyelectrolytes, forming an agglomerated mass consisting essentially of the negatively charged polyelectrolyte and the acid-treated colloidal particulates.

According to yet another aspect of the present invention, there is provided a base-treated, resuspendable, colloidal particulates, having a maximum particle size below 0.2 microns, which bind directly to positively charged polyelectrolytes, forming an agglomerated mass consisting essentially of the positively charged polyelectrolyte and the base-treated colloidal particulates.

DETAILED DESCRIPTION OF THE INVENTION

It is hypothesized that magnetic materials, in particle form, tend to have significant surface polarity, which is minimized by agglomeration of crystals of such materials. When these crystal agglomerates are subdivided or disrupted, they tend to become unstable, again forming crystal agglomerates over time. In accordance with the present invention, the nascent (and probably charged) surfaces of these sub-particles are stabilized by the coating material which may be deposited simultaneously or sequentially on these surfaces as the parent particles are sub-divided or thereafter, but before crystal agglomerates begin to form.

For that purpose, the coating material may be chosen on the basis of its tendency to respond to the surface polarity of the deagglomerated magnetic particle and various coating materials will thus react differently with different particulate magnetic materials. If the treating or disrupting technique is, or includes, pH modification, the effect of pH modification on sub-particle surface polarity and coating material polarity may also be a consideration. The coating material is selected in each case with regard to its ability to adhere to, or be adsorbed on or otherwise modify a property of the surface of the deagglomerated or sub-divided particle so that the stability of the particle product of reduced size is retained, to provide a stable suspension thereof.

This invention provides significant advantages over Molday and Owen et al. for preparing colloidal materials beyond the inherent simplicity of the method. For example, if it is desired to attach compounds to metal oxide particles where the compound has reactive groups or activated groups for subsequently attaching other materials, such as antibodies or enzymes, the Molday and Owen et al. procedures are limited insofar as the choice of such compounds is concerned. This is because these processes necessarily start by mixing such compounds with metal chlorides which themselves can react with the compounds and which also create acidic pH. Further, base addition, usually ammonium hydroxide, is required to form the metal oxides and can clearly have deleterious effects on a variety of activated chemical groups used for the subsequent coupling. By contrast, the direct adsorption methods of this invention, are subject to no such limitations. Furthermore, the coating process of this invention can be performed under non-aqueous conditions or in systems in which water is a minor component, thereby enabling the use of coating materials having limited aqueous solubility.

Certain types of coatings, such as the long chain hydrocarbons suggested in the Papell patent, have a detergent effect. Such coatings can serve to stabilize the subdivided deagglomerated magnetic particles and produce a stable suspension, such as that taught in Papell. In accordance with the present invention, these suspensions are produced, from magnetite and with sonication as the disrupting means, several orders of magnitude faster than in the ball milling process described by Papell.

To produce resuspendable products, it is important to select a coating material which not only stabilizes the sub-divided magnetic particles, but does so with a coating which remains intact when the coated particles are removed from suspension, which is not the case with Papell.

Magnetic compounds which may be used as the starting material in the present invention include the transition metal oxides, sulfides, silicides and carbides, optionally having different transition metals in a single magnetic compound, such as $Gd_3Fe_5O_{12}$. Preferred is the class of magnetic oxides known as ferrites, generally represented as $MO.Fe_2O_3$ in which M is Zn, Gd, V, Fe, In, Cu, Co, Mg, in particular magnetite ($FeO.Fe_2O_3$).

In addition to the transition element-containing compounds taught by Owen et al. and the ferrites noted above, a class of magnetic metal oxide which does not contain iron can be coated as described in this invention. These compounds include oxides of combinations of two or more of the following metal ions: $Al(+3)$, $Ti(+4)$, $V(+3)$, $Mb(+2)$, $Co(+2)$, $Ni(+2)$, $Mo(+5)$, $Pd(+3)$, $Ag(+1)$, $Cd(+2)$, $Gd(+3)$, $Tb(+3)$, $Dy(+3)$, $Er(+3)$, $Tm(+3)$ and $Hg(+1)$. They differ from ferrites in both appearance and magnetic susceptibility. The non-ferrites can take any color from white or yellow to green and even brown. This makes them particularly useful in spectrophotometric applications. Non-ferrites are generally less strongly magnetic than ferrites and, as such, pass through HGMS filters in magnetic fields capable of collecting ferrite based materials which permits selective magnetic retrieval.

The non-ferrous oxides can be employed in place of the metal oxides described by Whitehead et al. to produce silane coated magnetic particles which have the desirable properties given above. Similarly, when the chlorides (or sulfates) of such combinations are employed according to the methods taught by Molday or by Owen et al., coated product having very desirable magnetic and spectral properties can be obtained.

As indicated above, coating materials which may be used are preferably in aqueous suspension or solution, although suitable coating materials in non-aqueous liquid media or in the form of melts may also be used. The coating material is usually a synthetic or natural polymer and may be a protein or a nucleic acid. In principle, however, the coating material can be any substance which has affinity for the surfaces of such crystals.

In carrying out the process of the invention involving disruption of the particulate magnetic starting material in the presence of the coating material, the two materials are combined in a liquid mixture, usually including a liquid third component, such as water, to form a suspension. The relative proportions of these materials in this mixture is not critical. However, in general, the proportion of magnetic particles to coating material is from 1000:1 to 1:10 (by weight).

To make stable suspensions of coated sub-particles of the magnetic starting material, the mixture may be treated in a number of ways to disrupt or sub-divide the magnetic particulate starting material. These include mechanical and chemical means, such as heat, vibration, irradiation, sonication, pH modification, or a combination of these. Of these, sonication is particularly preferred.

In investigating means for disrupting or sub-dividing the magnetic particulate starting material, it has been discovered that, even in the absence of coating material, starting material can indeed by divided into smaller size particles, albeit generally in a transitory condition insofar as stability is concerned. From this observation, it has been established that if coating material is added to a suspension of the smaller size particulate magnetic substrate in a suitable liquid medium, following division of the magnetic starting material and before substantial particulate magnetic substrate aggregation occurs, i.e., while the smaller size magnetic particles remain stably suspended, resuspendable coated magnetic particles can be produced. By "substantial particulate magnetic substrate aggregation" is meant that a substantial number of particles are no longer in their most finely divided state, as evidenced, in some cases, by a change in the appearance of the suspension from shiny to dull, which is indicative of particle aggregate formation. Alternatively, the occurrence of substantial particle aggregation can be determined by means of quasielectric light scattering, when the average particle size is shown to increase significantly from its minimum size.

Coating materials can also be added sequentially after the disruption process such that material of particular interest is first added to the sub-divided material in a limited amount and allowed some time to adhere to the particulate substrate. The exact time will depend upon how long crystal reaggregation takes under the conditions of exposure to the specific coating material selected. Next, a different coating material whose essential functions are to coat portions of disrupted crystals left bare by the primary coating and to prevent agglomeration is added so as to stabilize the system. Various disperson aids may be used for this purpose. Suitable dispersion aids include, for example, conventional detergents, anionic, cationic and/or non-ionic surfactants, and the like. The selection of an appropriate dispersion aid will depend on the nature of the surface charge on the colloidal magnetic particles. The dispersion aid serves to help stabilize the colloidal, magnetic particles in suspension.

The sequential coating approach enables the uptake of coating material of interest to be maximized and in many cases substantially complete particle coating can be achieved. In this way, the amount of the primary coating material can be limited, allowing the coating process to be performed without the need for subsequent purification of unbound primary coating material from the desired coated magnetic particle product. Additionally, by carefully controlling the concentration and/or timing of subsequently added coating material, stable agglomerates of different size can be obtained. Another advantage of adding coating materials after disaggregation of the particulate magnetic starting material is that any adverse effect that the disruption process may have on the coating materials will be avoided. Further, the latitude of carrying out the coating operation in two distinct steps has a variety of obvious process advantages for particular situations.

We have also discovered that the employment of high gradient magnetic separation (HGMS) in the production of such particles gives a dimension to their production which heretofore has not been achieved or recognized. The Molday and Owen et al. processes utilize either centrifugation, gel filtration or "salting out" as manipulative procedures during the processing of colloidal materials. In the example herein, HGMS has been used to separate colloidal particles from unbound coating substance. In processes where it might be desirable to chemically couple substances to such particles, HGMS offers process facilitation which is readily scaled and highly efficient.

HGMS can also be used in concert with tuned magnetic fields to fractionate preparations based on their magnetic susceptibility/particle volume ratios. This permits convenient fractionation and production of particle preparations of discrete sizes. When used as NMR contrast agents, the size of the particle plays an important role in the metabolic fate of the material. HGMS, again with tuned magnetic fields, can also be used to selectively capture particles where the magnetically responsive core contains transition element oxides having higher magnetic susceptibilities than others in the mixture. This concept could have utility in a system whereby colloidal particles having different magnetic susceptibilities as well as different bioreceptors could be mixed with a sample and removed by sequential HGMS using increasing gradient field strength.

Not only can HGMS be used to separate unadsorbed coating or unreacted substances and by-products from the colloidal, magnetic particle product, it can also be utilized for immobilizing coated magnetic products and performing reactions on the immobilized material. Thus, if it is desired to chemically modify a given coating, reactants can be added to magnetically immobilized material, the reaction performed in that state and excess reactant or other reaction products easily washed away. This concept, somewhat like peptide synthesis done on solid supports, lends itself nicely to sequential reactions.

Although the foregoing methods of the invention have been characterized as coating methods, such methods may aptly be considered extraction methods, depending on the particular application. Thus, the methods described herein may be beneficially utilized for the specific purpose of extraction of a target material from a complex mixture, such as isolation of environmentally hazardous materials from a waste stream, product recovery from a reaction mixture or the separation of a component of value from a mixture comprising generally worthless components.

Another application of the present invention which is in the nature of an extraction is the method of binding polyelectrolytes, e.g., nucleic acids, to colloidal magnetic particles. This method involves the use of the chemically-treated, resuspendable, colloidal magnetic particles for selectively binding to polyelectrolytes, e.g., DNA or RNA as a means for extracting such target molecules from a complex mixture. The ability of such resuspendable, colloidal magnetic materials to bind to polyelectrolytes, as well as the enormous surface area of such materials, coupled with their ability to be magnetically retrieved affords significant benefits when so used. This binding agent is conveniently prepared by subdividing the particulate magnetic starting material into a plurality of resuspendable, smaller sized particulates which are treated with a chemical agent that imparts the desired surface charge to such particulates. Disruption techniques such as sonication or pH adjustment may be used for this purpose, the former being preferred. Sonication not only produces disaggregation of the particulate magnetic starting material, but may also be used to cause simultaneous disruption of certain biological entities, such as cells or bacteria, whose contents includes the target molecule. Upon release via sonication, the target molecule becomes bound to the resulting colloidal magnetic particles, provided they have been subjected to appropriate chemical treatment.

In carrying out this process, the particulate magnetic starting material may be disrupted to form a transient colloid, as described herein, to which a test sample containing the target molecule to be bound is subsequently added, or the particulate magnetic starting material can be disrupted in the presence of the target molecule.

The examples set forth below demonstrate that treatment of subdivided magnetic particulates with various chemical agents, such as acid or base, for adjustment of pH (or ionic strength), markedly affects binding selectivity for various polyanions and polycations. Thus, it is clear that as a means for performing extraction, this procedure offers considerable specificity for the polyelectrolyte of interest. By adjusting solvent, buffer and salt conditions after the binding step and after the bound polyelectrolyte material has been magnetically separated, the target polyelectrolyte is readily recoverable in biologically active form. After recovery of the target polyelectrolyte, the particulate magnetic material may be recycled.

It should be appreciated that this process will function even with transition element oxides materials which have relatively low magnetic susceptibility properties as described hereinabove. In those cases where the material used for polyelectrolyte capture is not sufficiently magnetic for magnetic separation to be effective, filtration could be used for separation and subsequent recovery.

The following examples will serve to illustrate the principles of this invention; however, these examples should not be construed as limiting the scope of this invention.

EXAMPLE 1

All reagents and chemicals used in these experiments were of analytical grade and obtained from Fisher Scientific (Valley Forge, Pa.) unless otherwise specified. Magnetite was prepared by mixing solutions of 3.0 and 1.5 mg/ml of ferric chloride hexahydrate and ferrous chloride tetrahydrate, respectively, with stirring at room temperature while raising the pH to 8.6 with NH₄OH. The resultant magnetite was collected magnetically, washed 3 times with distilled water and resuspended in distilled water. The preparation so made contained 1.5 mg/ml magnetite. Even after sonication (Fisher - Sonic Dismembrator Model 300) for 3 minutes at 70% output, these preparations will not remain suspended for more than about 2 minutes.

To coat magnetite particles by the method of this invention, 0.5 ml aliquots of various concentrations of various coating materials were mixed with 0.5 ml aliquots of the 1.5 mg/ml magnetite suspension. Samples were mixed in conical plastic centrifuge tubes and subsequently sonicated for 3 minutes at 70% output at room temperature. A positive or partially positive coating result was apparent from visual inspection of the manner in which light was scattered by the sample.

To determine the efficiency of coating, resultant samples were further observed for settling and also were fractionated into colloidal coated magnetite or microagglomerates thereof in the following fashion: 0.5 ml aliquots of the sonicated mixture in 12×75 mm test tubes were placed in a Ciba-Corning Magnetic Separator (Walpole, Mass.) and visually observed. The criterion used to determine if the coated magnetite crystals were colloidal was to observe if the resultant material remained in solution in the magnetic separator for a period of 10 minutes, i.e., in the magnetic supernatant. This criterion was established on the basis that solutions of protein coated colloidal magnetite prepared by the process of Owen et al. could not be separated magnetically in the Magnetic Separator when placed therein for such periods.

To determine what portion of the sonicated mixtures formed stable, coated, but agglomerated materials which pulled to the sides of the test tubes in the Magnetic Separator, materials so formed were washed with 20 mM phosphate three times and resuspended in the same buffer. Their resuspension characteristics compared with uncoated magnetite were distinctly different, as they would remain suspended for hours compared with minutes for the latter.

A second criterion involved examining the magnetic supernatant as follows: Putative colloidal material was separated from the mother liquor by HGMS, washed, and resuspended in buffer, and visually observed for colloidal appearance and stability. HGMS was accomplished by placing approximately 20 mg of fine grade stainless steel wool (McMaster-Carr, New Brunswick, N.J.) (washed in detergent, incubated in 1% BSA phosphate buffered saline (PBS), rinsed with deionized water, dried and cut in approximately 3 mm lengths) into 12×75 mm glass test tubes. 100 microliters of the supernatants to be tested were added to the test tubes containing the stainless steel wool and placed in the magnetic separating rack for 2 minutes by which time magnetic material had collected on the stainless steel wires. Clear non-magnetic supernatants were removed with Pasteur capillary pipettes and the magnetic material washed 3 times with 300 microliters of 20 mM phosphate (pH 7.5). After the third wash, collected magnetic material was resuspended in the phosphate buffer, after removing the tube from the magnetic rack, and examined visually for the appearance of a stable colloid.

In some instances recovered material was also sized by laser light scattering (Coulter Sub Micron Particle Analyzer N4SD, Hialeah, Fla.). Some supernatants were separated from unadsorbed material by gel filtration chromatography on Sephacryl-300 (Pharmacia) or ultra gel AcA-22.

Table I lists different compounds used in coating experiments, their concentration(s), and other solvent conditions. The presence and semi-quantitation of colloidal and agglomerated materials were determined visually by the procedures described above, by comparison to standards prepared from known mixes of colloidal and agglomerated stocks. As can be seen from Table I, every compound tested produced some amount of stable colloidal material. Where noted, stability, following HGMS and resuspension in phosphate buffer, is also indicated. In all cases the success of the coating experiment could be determined immediately following the sonication procedure from light scattered or by the apparent "shininess" of the solution. Materials for which coating conditions were inappropriate (i.e., stable coated subdivided particles were not produced) were by contrast dull and heterogeneous in appearance.

TABLE I

| Supernatant Coating Material and Concentration (wt %) | Percent Colloidal | HGMS Recovery | Treatment of Colloidal Subsequent Resuspension |
|---|---|---|---|
| Dextran, 25% | 100% | Good | Good |
| Dextran, 12.5% | 50% | Good | Good |
| Dextran, 6.25% | 25% | ND | ND |
| Dextran, 3.12% | 50% | ND | ND |
| SDS, .5% | 5% | ND | ND |
| SDS, .25% | 20% | ND | ND |
| SDS, .125% | 80% | Good | Poor |
| SDS, .063% | 50% | ND | ND |
| Tween-20, 1% | 20% | Good | Fair |
| Tween-20, .5% | 30% | ND | ND |
| Tween-20, .25% | 40% | ND | ND |
| Tween-20, .125% | 50% | ND | ND |
| Tween-20, .063% | 75% | ND | ND |
| Tween-20, .031% | 90% | ND | ND |
| Tween-20, 3.5% | 50% | ND | ND |
| BSA, 1% 50 mM P | 95% | Good | Good |
| BSA, 7.5%; 50 mM P | 80% | ND | ND |
| BSA, 7.5%; 40 mM P | 75% | ND | ND |
| BSA, 7.5%; 30 mM P | 50% | ND | ND |
| BSA, 7.5%; 20 mM P | 90% | ND | ND |
| BSA, .25%; 016% Tween-20 | 95% | Good | Good |
| IgG(human), 5%; PBS, 50% | 60% | Good | Good |
| Lipid Stripped Human Sera | 100% | Good | Good |
| G α MFc/50 mM P 1:2 | 5% | ND | ND |
| G α MFc/50 mM P 1:4 | 50% | ND | ND |
| G α MFc/50 mM P 1:8 | 5% | ND | ND |
| G α MFc/50 mM P 1:16 | 30% | ND | ND |
| G α MFc/50 mM P 1:32 | 20% | ND | ND |
| G α MFc/50 mM P 1:64 | 5% | ND | ND |
| Steroid Free, Lipid Stripped Sera, Neat | 5% | ND | ND |
| Steroid Free, Lipid Stripped Sear/50 mM p (1:128) | 50% | ND | ND |
| PEG, 20% | 80% | ND | ND |
| GLA, 10% | 100% | ND | ND |
| poly G, 10% | 15% | ND | ND |
| polyvinyl pyrrolidone, 15% | 75% | ND | ND |
| polyvinyl alcohol, 10% | 50% | ND | ND |

ND = Not Done
P = Phosphate buffer
G α Mfc = goat anti-mouse Fc [Jackson Labs, West Grove, PA]
SDS = sodium dodecyl sulfate

TABLE I-continued

| Supernatant Coating Material and Concentration (wt %) | Percent Colloidal | HGMS Recovery | Treatment of Colloidal Subsequent Resuspension |
|---|---|---|---|

PEG = polyethylene glycol [Matheson, Coleman and Bell, East Rutherford, NJ]
Dextran = Dextran T-40 [Pharmacia, Piscataway, NJ]
poly G = polyglutamic acid [NEN, Pilot Chemical Division, Boston, MA]
GLA = [(glutamic acid 45 mole %) (lysine 35 mole % (alanine 20 mole %)]$_n$ [NEN, Pilot Chemical Division, Boston, MA]
IgG = Immunoglobulin G Lipid stripped and steroid free lipid stripped sera from Scantibodies Inc., Santee, CA
Tween-20 = Polyoxyethylene surfactant (ICI Americas)

EXAMPLE 2

Quantitation of Protein Coating and Retention

I-125 labeled BSA and IgG were prepared by the Iodogen method of Fracker and Speck (Biochem. Biophys. Res. Comm. 80 849, (1978)). Specific activities were 520,000 cpm/μg and 810,000 cpm/μg, respectively.

BSA was coated onto magnetite under two sets of conditions as follows (1) at 7.5% BSA in 10 mM phosphate buffer followed by 3 minute sonication and (2) at 7.5% BSA in 25 mM phosphate buffer followed by 3 minute sonication. In both cases 800,000 cpm of labeled BSA was added to the mixture (0.5 ml) prior to sonication. From visual inspection it was apparent that the higher concentration of phosphate resulted in significantly more colloidal material. The magnetically collectable precipitate for each experiment was collected, washed twice in 20 mM phosphate buffer and counted. The magnetic agglomerated material of conditions 1 and 2 contained 2421 and 2828 cpm, respectively. To determine how well BSA had adsorbed to these agglomerated preparations the recovered material was suspended in 0.1 M glycine at pH 3.0 for 40 minutes at room temperature, magnetically separated and washed once with 20 mM phosphate buffer. For experimental conditions 1 and 2, counts retained were respectively 91 and 84%. When similar preparations were resuspended in buffer and allowed to incubate over night at 37° C., no material desorbed from the magnetite.

To determine the stability of the colloidal magnetite BSA, the amount of BSA adsorbed onto the colloid was quantified as follows: 3×100 μl aliquots of the supernatant were individually collected by HGMS, washed two times with 300 μl of phosphate buffer and resuspended into 100 μl of the same buffer. By observation over time (16 hours) it was apparent that the colloidal material was stable. Radioactive BSA recovered by HGMS for the total supernatant was 5400 cpm. From radioactivities and volumes of the supernatant and agglomerated materials obtained for condition 2 it was determined that 7,828 cpm's had been incorporated onto magnetite. This amounts to 0.01% of the total BSA added to the system which corresponds to about 0.75 mg/ml of magnetite so prepared. This value is very close to the optimal amount of BSA which can be coated onto magnetite by the procedure of Owen et al.

The IgG coating experiments were done at 5% protein concentration in PBS/2 (a 1:2 dilution of PBS in $H_2O$). Before sonication, mixtures were spiked with $1.8 \times 10^6$ cpm of radio labeled IgG. For these experiments it was found that 1.2% of the total added protein was adsorbed which corresponds to 1.2 mg IgG/ml of magnetite. Again this is close to the maximum coating obtainable by the Owen et. al. teaching. When HGMS was performed on the magnetic supernatant of this experiment 23,000 cpm were retained on the colloidal material. The agglomerated magnetic pellet retained 17,300 cpm's after multiple washings. When the magnetic pellet was resuspended in glycine at pH 3.0 as above only 50% of the counts were retained on the subsequent magnetic pellet. However, in these experiments it was found that glycine treatment of the microagglomerated material had converted a substantial portion (approximately half) to colloidal material; hence, the IgG coated material is indeed stable. Colloidal materials recovered by HGMS were stable by visual observation.

EXAMPLE 3

Retention of Biological Activity

Goat anti-mouse Fc (obtained from Jackson Laboratories, West Grove, Pa.) was coated onto magnetite as described in Example 1. For coating, the untreated anti-sera was diluted 1:4 with 50 mM phosphate. After the sonication procedure, most of the resultant material appeared colloidal. The entire supernatant was separated on Sephacryl-300. Colloidal material appearing in the void volume was recovered and the following test performed: 100 ul of the recovered colloid was mixed with either 100,000 counts of 125-I labeled mouse IgG or 100,000 counts of 125-I BSA. These mixtures were incubated in 12×75 mm tubes in the presence of iron powder as described above. After 90 minutes at room temperature, HGMS was performed, as described above, supernatants were discarded, and collected material washed twice with 0.8 mls of PBS containing 2% BSA. For these colloid samples (in triplicate) it was found that, on average, 5,200 counts of mouse IgG was bound to the Fc-coated colloid versus 632 cpm of nonspecifically bound BSA.

EXAMPLE 4

Light Colored Particles

Mixed transition metal oxides were prepared at room temperature and at 65° C. by addition of base to appropriate metal chlorides as described in Example 1. Table II lists preparative conditions, molar ratios, initial color of the oxides and color after 1 week, or color after bubbling $O_2$ through freshly prepared oxides for eight hours.

TABLE II

| | Concentration (mMole/Liter) | | | | | | | |
|---|---|---|---|---|---|---|---|---|
| Part. | $FeCl_2$ | $VCl_3$ | $CoCl_2$ | $PdCl_3$ | $DyCl_3$ | $ErCl_3$ | Original Color | Final Color* |
| 1 | — | 5 | — | — | 5 | — | dk green | white |
| 2 | 2.7 | 3.6 | — | — | 3.6 | — | dk green | yellow |
| 3 | 5 | 3.3 | — | — | 1.7 | — | dk green | orange |

TABLE II-continued

| Part. | FeCl$_2$ | VCl$_3$ | CoCl$_2$ | PdCl$_3$ | DyCl$_3$ | ErCl$_3$ | Original Color | Final Color* |
|---|---|---|---|---|---|---|---|---|
| 4 | 6 | — | — | — | 4 | — | dk green | rust |
| 5 | — | — | 5 | 5 | — | — | green | brown |
| 6 | — | — | — | 5 | 5 | — | brown | brown |
| 7 | — | 5 | 5 | — | — | — | blue/green | green |
| 8 | — | 5 | — | — | — | 5 | lt brown | white |
| 9 | — | — | — | 5 | — | 5 | brown | brown |
| 10 | — | — | — | — | 5 | 5 | white | white |
| 11 | 5 | — | — | — | — | 5 | green | orange |

*These oxides change color gradually in about one week, or in about eight hours if the new precipitate is bubbled through with oxygen.

Table III lists the results of coating the oxide preparations of Table II (preps 1, 2, 3 and 4) with dextran and with BSA, according to the method of this invention. Clearly these materials can be coated similarly to magnetite. It is noted that the non-ferrite and ferrite oxides listed in Table II could be used in place of magnetite with the teaching of Whitehead et al. to produce similarly colored silane coated materials. When the appropriate chlorides (or sulfates) of these metals are used with the teachings of Molday or with Owen et al., it is possible to obtain colloidal materials which are nearly transparent in the visible region.

TABLE III

| | | Appearance After Sonication | | |
|---|---|---|---|---|
| Particle | Compound | Supernatant | Pellet | % Colloidal |
| 1 | 25% Dextran | Shiny White | White | 90% |
| 2 | 25% Dextran | Cloudy Yellow | White | 20% |
| 3 | 25% Dextran | Clear Yellow | White | 95% |
| 4 | 25% Dextran | Clear Orange | Orange | 50% |
| 1 | 1% BSA/50 mM P | Shiny White | white | 90% |
| 2 | 1% BSA/50 mM P | Cloudy | White Yellow | 90% |
| 3 | 1% BSA/50 mM P | Clear Yellow | White | 95% |
| 4 | 1% BSA/50 mM P | Clear Orange | Orange | 75% |

EXAMPLE 5

Colloid Particle Size

BSA magnetite was prepared with the magnetite of Example 1 and BSA at 1% in 50 mM Phosphate at pH 7.0 as described above except that an aliquot was sonicated for a second three minute period and another for a third three minute period. After removal of any agglomerated material with the magnetic rack, as described above, the resultant colloidal samples were sized by laser light scattering (Coulter Submicron Particle Analyzer). Within experimental error each preparation had a mean particle diameter of 80 nm.

Next, magnetite for coating was prepared by two methods which have been found to decrease particle size in the Owen et al. procedure, namely very rapid addition of base and very rapid addition of base at elevated temperature (65° C.). When BSA magnetite was prepared with a single 3 minute sonication step but with magnetite prepared according to Owen et al., the resultant colloids were both of 50 nm mean diameter.

EXAMPLE 6

Properties of Magnetite as Affected by pH 3.75% NH$_4$OH was added at 0.6 mls/minute to a 200 ml stirred mixture of degassed hydrated ferric and ferrous chloride salts at 7 and 3 mg/ml respectively. As the pH of the initially acidic mixture approached 7.0 (indicted by a color transition from dark orange to black), 300 ul aliquots were removed, placed in 10×75 glass test tubes, and tested for the presence of magnetite, by placing a neodymium/iron/boron bar magnet to the side of the tube and visually observing magnetic clearing. The transition from non-magnetic or partially magnetic material to totally magnetic material occurred at pH 7.4 after 12.2 mls of base had been added. At this point, 60 ml of the mixture was removed and designated preparation A. Additional base was added to the mixture to pH 8.9; a 60 ml aliquot was removed and labelled preparation B. Base was further added to the reaction mixture to pH 9.8 and an aliquot of this material designated preparation C. Magnetite preparations A, B, and C were washed 4 times with distilled water and resuspended in water such that the iron salts were at the starting concentrations of the original solution. 0.5 ml aliquots of the latter suspensions of A, B and C were sonicated for 3 minutes at 70% output (Fisher Sonic Dismembrator). Immediately following sonication, each had the shiny appearance of colloidal magnetite; however, all reverted to dull suspensions (indicative of particle aggregates) within 2 minutes. For preparation C, the transition occurred 20–30 seconds following sonication; for preparation B, 40–50 seconds; while preparation A required 2 minutes for this transition. When the preparations were placed in the Corning magnetic rack immediately following sonication, they cleared completely from suspension in the same order as above and over the same time frame. After reaggregation, there was no discernible difference among the samples.

To determine if prepared magnetites' susceptibility to dissociation by sonication is altered by H$^+$ or OH$^-$ treatment, 0.5 ml aliquots of the preparation C suspension were placed in test tubes and separated from their water supernatants by magnetic separation and supernatant aspiration. Magnetic pellets were then resuspended into 0.5 ml of either dilute HCl (0.1, 0.01, 0.001, or 0.0001 M) or dilute NaOH (0.1, 0.01, 0.001, or 0.0001 M), sonicated for 3 minutes as above and visually inspected. For these samples, it was apparent that acid or base treatment increased the disruption of magnetite in proportion to concentration of acid or base. The aliquots resuspended and sonicated in 0.1 M HCl or NaOH remained shiny, i.e. colloidal, for nearly 12 hours. The aliquots resuspended in 0.001 M acid or base also exhibited colloidal behavior for significant periods of time. On the other hand, aliquots resuspended into 0.0001 M acid or base quickly aggregated after sonication much like the parent material did in water.

EXAMPLE 7

Coating of pH Modified Magnetite

Preparation C of Example 6 was coated by disruption via sonication with anionic and cationic polypeptides. An anionic terpolypeptide composed of 60 mole % glutamic acid, 30 mole % alanine, 10 mole % tyrosine (GAT, Lot #M18G) and a cationic copolymer of 60 mole % lysine, 40 mole % alanine (LA, Lot #M-5B), both obtained from Pilot Chemicals, Watertown, Mass., were used. These polypeptides, both of about 100,000 Daltons, were solubilized by trituration with appropriate acid or base, neutralized, dialyzed versus phosphate buffered saline (pH 7.0) and subsequently against distilled water. Coatings were attempted with 10 mg/ml solutions of polypeptide and serial dilution of same to 1/16. Coating experiments were done by sonication as described above. For these experiments, the 1/16 and 1/8 dilutions of both GAT and LA produced stable colloidal solutions. The 1/4, 1/2 and undiluted polypeptide solutions resulted in distributions of colloid and agglomerated material. The amount of colloid both instances generally decreased with increasing polypeptide concentration. However, at 25 mg/ml GAT all of the material was colloidal.

Preparations A and C of Example 6 were coated with GAT. 0.5 ml aliquots of magnetite were resuspended in 1.0 ml of HCl (0.01 and 0.1 M) or NaOH (0.01 and 0.1 M) for 60 seconds followed by two 0.5 ml water washes. These pre-treated magnetites were resuspended in 0.5 ml aliquots of 1 mg/ml GAT containing $2.5 \times 10^6$ cpm $^{125}I$GAT (radiolabeled by the Iodogen method described above) and sonicated as described. Sonicated samples were placed in the Corning magnetic rack and left to separate overnight. Magnetic pellets were washed once in 0.5. M NaCl and counted. Counts bound and percentages of GAT coated onto the various magnetites are given in Table IV.

TABLE IV

Effect of H+/OH− Treatment of Magnetite Preparations A and C on GAT Coating

| Treatment | Preparation A | | Preparation C | |
|---|---|---|---|---|
| | cpm bound | % bound | cpm bound | % bound |
| 0.10 M HCl | 450,000 | 35 | 340,950 | 26 |
| 0.01 M HCl | 287,602 | 22 | 226,250 | 17 |
| H₂O Control | 209,165 | 16 | 236,042 | 18 |
| 0.01 M NaOH | 130,728 | 10 | N.D. | N.D. |
| 0.010 M NaOH | 90,600 | 8 | 54,010 | 5 |

N.D. = Not done

From the data of Table IV, it is clear that magnetite crystal surface charge can be made more positive by a pre-treatment with acid and conversely, treatment with base generally reduces sites available to the negatively charged polymer. When $^{125}I$ preparation of the cationic terpolymer LAT (60 mole % lys, 30 mole % ala, 10 mole % tyr), (received from Dr. H. J. Callahan, Jefferson Medical College, Philadelphia, Pa.) was used with similarly pre-treated magnetite, it was observed that greater binding of this positively charged material occurred on magnetite pre-treated with base.

To determine if crystal surface charge alteration via acid or base treatment is a general property of transition element oxides, such as those prepared from different molar ratios of chlorides of Fe (II), Dy (III), V (III), such materials were treated with acid or base as above and mixed with either radio-labelled GAT and/or Salmon sperm DNA (Sigma Chemical Co., St. Louis, Mo.). As in the case with magnetite, acid treatment promoted binding of these negatively charged polyelectrolytes. In fact, uncoated materials pre-treated with 0.1 M HCl, followed by water wash on sonication give materials which behaved like preparations of magnetite described above, i.e., transiently stable colloids. When these materials were in this semi-stable colloid state, addition of Salmon sperm DNA in appropriate quantities lead to complete agglutination indicating the crystals had assumed substantial positive surface charge.

EXAMPLE 8

Post Sonication Direct Coating

Magnetic ferrofluid was prepared by the addition of coating material after sonication of the bare magnetite according to the procedure described below.

The bare magnetite was prepared by the process as described in Example 1, above. The magnetite was separated from water by a bar magnet and resuspended in phosphate buffer of pH 7.5. The average particle size of the magnetite was reduced by pulsed sonication (Fisher's Sonic Dismenbrator 550) for five minutes, using 10 second pulses and 10 second pauses in succession.

Immediately following sonication, the first coating material, i.e., 1 mg/ml 9x biotin-BSA in 20 mM phosphate buffer at pH 7.5, was incubated with the sonicated bare magnetite for a period of 15 minutes at room temperature. The second coating material, i.e., 5 mg/ml BSA in 20 mM phosphate buffer at pH 7.5, was added to the mixture of magnetite and first coating material.

Table V shows the effect of varying coating concentrations on the colloidal magnetic particle size over time and the separation rates in a high gradient magnetic field. The particle size was measured by Coulter Sub-micron Particle Analyzer (Model N4SD). The magnetic properties of the colloidal particles were determined by high gradient magnetic separation in a 300 μl microtiter well with grids in a 4 kG uniform magnetic field.

TABLE V

Effect of Concentration of Primary and Secondary Coatings on Stability and Separation Rate of Colloidal Magnetic Particles

| [1° Coating] | [2° Coating] | Particle Size* (nm) | | | % Separation | |
|---|---|---|---|---|---|---|
| (mg/ml) | (mg/ml) | 0 | 24 | 168 (hrs) | 30 | 60 (sec) |
| 0.0 | 5 | 106 | 66 | 68 | 70 | 90 |
| 0.1 | 5 | 74 | 83 | 86 | 80 | >90 |
| 0.3 | 5 | 77 | 81 | 83 | 81 | >93 |
| 0.5 | 5 | 76 | 83 | 85 | 85 | >95 |
| 0.7 | 5 | 78 | 83 | 82 | 88 | >95 |

*For the duration of the stability test, all colloidal magnetic particles remained clear and in suspension.

EXAMPLE 9

Preparation of Stable, Colloidal Magnetic Particles by Direct Coating of Biotinylated BSA with Simultaneous Sonication Stable, colloidal magnetic particles were prepared by simultaneous size reduction of particulate magnetic starting material and coating during sonication.

The bare magnetite was prepared by the process as described in Example 1, above. The magnetite was separated from water by a bar magnet and resuspended in 1 mg/ml 9x biotin-BSA in 20 mM phosphate buffer of pH 7.5. The average particle size of the magnetite was reduced by pulsed sonication (Fisher's Sonic Dismenbrator 550) for one minute, using 10 second pulses and 10 second pauses in succession.

The particle size and the magnetic separation rate was measured as described in Example 8, above.

The average particle size was 80 nm. The separation rate was 85% in 30 seconds and >95% in one minute. The resultant product was monitored over a period of two weeks and was found to be stable, as the direct coated magnetite remained in suspension and was clear in appearance.

EXAMPLE 10

Binding and Removal of DNA From Solution Using Uncoated Colloidal Magnetic Particles This example shows that pure λ DNA can be bound and recovered using bare, uncoated colloidal magnetic particles under acidic conditions.

The colloidal magnetic particles were prepared by magnetically sedimenting suspensions of bare magnetite prepared as in Example 1, in water at a level of 1 mg iron/ml solution. The magnatant (non-sedimented liquid phase) was aspirated and resuspended in 0.1 M NaCl to a volume equal to the original. The suspension was vortexed for five seconds and then washed three times successively with deionized water. During each wash, the magnetite was held in place magnetically.

Two test samples of DNA fluorescently labelled with Hoechst dye H33258 (LIFE TECHNOLOGIES catalogue #5250SB) were prepared. The first sample, Sample A, was made up by adding 1 ml of 8 μg/ml λ DNA in 20 mM phosphate buffer at pH 5 immediately to a first test tube with agitation. The resultant mixture was then sonicated in the tube on ice using microtip probe for one minute (Fisher Sonic Dismembrator, model 550; setting 3, pulse cycle 1 second on/1 second off). The second sample, Sample B, was subjected to the same protocol, except that one ml of 8 μg/ml λ DNA in 20 mM phosphate buffer at pH 7.5 was used.

Amount of DNA was assayed by fluorometry, by comparing the amount of fluorescence before and after magnetic separation. Table VI shows the fluorescent signals and calculated % DNA removed from solution by binding to the colloidal, magnetic particles.

TABLE VI

Effect of pH on DNA Extraction from Solution

| Sample | pH | Fluorescence before M.S. | Fluorescence after M.S. | % DNA Capture |
|---|---|---|---|---|
| A | 5 | 60 | 29 | 52 |
| B | 7.5 | 60 | 63 | 0 |

EXAMPLE 11

Binding of DNA by Bare Magnetite and Recovery via Buffer Solution

This example shows that λ DNA captured under acidic conditions can be removed from bound colloidal magnetic particles by the selection of the wash buffer.

The magnetite and λ DNA were prepared as described in Example 10, above. Ten samples of the magnetite were prepared. All were sonicated with fluorescently labelled DNA under acidic conditions at pH 4 using 20 mM phosphate buffer. Initial fluorescent signal for the starting solution of DNA was 80. The DNA was magnetically pulled for 10 minutes and the supernatant was measured. From the difference between the starting fluorescence and the supernatant signal, the % DNA recovered was calculated.

Table VII shows that the percent extracted by sonication varied between 58 to 63%. The relative efficiencies of the wash buffers is shown as % recovery.

TABLE VII

Effect of Wash Buffer Type on DNA Removal from Ferrofluid

| Sample | First wash buffer | Second wash buffer |
|---|---|---|
| 1 | pH 9 Tris | pH 9 Tris + 200 mM NaCl |
| 2 | pH 9 Tris + 0.5% Polywet | pH 9 Tris + 1% Polywet |
| 3 | pH 9 Tris + 100 mM NaCl | pH 9 Tris + 500 mM NaCl |
| 4 | pH 10 CAPS | pH 10 CAPS + 200 mM NaCl |
| 5 | pH 10 CAPS + 0.5% Polywet | pH 10 CAPS + 1% Polywet |
| 6 | pH 10 CAPS + 100 mM NaCl | pH 10 CAPS + 500 mM NaCl |
| 7 | pH 4 Phosphate | pH 4 Phosph. + 200 mM NaCl |
| 8 | pH 4 Phosph. + 0.5% Polywet | pH 4 Phosph. + 1% Polywet |
| 9 | pH 4 Phosph. + 100 mM NaCl | pH 4 Phosph. + 500 mM NaCl |
| 10 | 1 N HCl | 1N NaOH |

| Sample | A | B | C | D | E | F | G | H |
|---|---|---|---|---|---|---|---|---|
| 1 | 32 | 48 | 60 | 12 | 25 | 13 | 27 | 52 |
| 2 | 31 | 49 | 61 | 16 | 33 | 11 | 22 | 55 |
| 3 | 31 | 49 | 61 | 19 | 39 | 0 | 0 | 39 |
| 4 | 33 | 47 | 59 | 16 | 34 | 5 | 11 | 45 |
| 5 | 31 | 49 | 61 | 15 | 31 | 11 | 22 | 53 |
| 6 | 33 | 47 | 59 | 13 | 28 | 2 | 4.3 | 32 |
| 7 | 34 | 46 | 58 | 3 | 6.6 | 2 | 4.4 | 11 |
| 8 | 30 | 50 | 63 | 15 | 30 | 12 | 24 | 54 |
| 9 | 40 | 40 | 50 | 10 | 25 | 1 | 2.5 | 28 |
| 10 | 31 | 49 | 61 | −25 | — | 17 | 35 | 35 |

A = Fluorescent signal of supernatant after a 10 minute separation.
B = Calculated Fluorescent signal. (Starting fluorescent signal of the labelled DNA solution = 80) −A.
C = % DNA extracted.
D = Fluorescent signal of supernatant after first wash.
E = % recovery from first wash.

TABLE VII-continued

Effect of Wash Buffer Type on DNA
Removal from Ferrofluid

F = Fluorescent signal of supernatant after second wash.
G = % recovery from second wash.
H = Total % recovery = E + G.

While certain embodiment of the present invention have been described and/or exemplified above, various other embodiments will be apparent to those skilled in the art from the foregoing disclosure. The present invention is, therefore, not limited to the particular embodiments described and/or exemplified, but is capable of considerable variation and modification without departure from the scope of the appended claims.

What is claimed is:

1. A process for making resuspendable, coated magnetic particles by direct application of a coating material to a particulate magnetic substrate, said process comprising:
   a. dividing at least one particle of a magnetic starting material into a plurality of aggregable, smaller sized particles, thereby to provide an uncoated particulate magnetic substrate;
   b. forming a suspension of said uncoated particulate magnetic substance in a liquid medium; and
   c. contacting said uncoated, suspended particulate magnetic substance with said coating material, before substantial particulate magnetic substrate aggregation occurs, for a time sufficient for said coating material to adhere to said substrate, thereby forming said resuspendable, coated magnetic particles.

2. A process according to claim 1, wherein said suspension is an aqueous suspension.

3. A process according to claim 1, wherein said magnetic starting material is a transition metal oxide.

4. A process according to claim 3, wherein said transition metal oxide is magnetite.

5. A process according to claim 1, wherein said coating material is a natural or synthetic polymer.

6. A process according to claim 1, wherein said coating material is a polypeptide, a protein, or an antibody.

7. A process according to claim 1, wherein said magnetic starting material is divided under the influence of irradiation, vibration, pH modification, or a combination thereof.

8. A process according to claim 1, wherein said magnetic starting material is divided by sonication.

9. A process according to claim 1, wherein said coated magnetic particles generally have a maximum dimension of less than 0.2µ.

10. A process according to claim 1, wherein said coated magnetic particles have a maximum dimension of less than 0.1µ.

11. A process according to claim 1, wherein the weight ratio of said particulate magnetic substrate to said coating material is from about 1000:1 to about 1:10.

12. A process according to claim 1, including the further step of recovering said resuspendable coated particles by high gradient magnetic separation.

13. A process according to claim 1, further comprising resuspending the magnetic coated particles in water or an aqueous buffer solution.

14. A process according to claim 13, wherein said resuspension is conducted under the influence of sonication.

15. A process according to claim 1, further including the step of reacting said coated magnetic particles with a bifunctional compound specific to said coating.

16. A process according to claim 1, further including the step of reacting said coated magnetic particles with a bifunctional compound adapted to form primarily intraparticulate bonds.

17. A process according to claim 1, further including the step of reacting said coated magnetic particles with a biofunctional compound and reacting the product particles with a bifunctional ligand.

18. A process according to claim 1, further including the step of reacting said coated magnetic particles with an activating agent and reacting the product particles with a biofunctional ligand.

19. A process for making a stable suspension of resuspendable magnetic particles, said process comprising:
   a. forming a liquid mixture of a particulate magnetic starting material;
   b. sonicating said mixture to divide said particulate magnetic starting material into a plurality of uncoated aggregable, smaller sized particles suspended in a liquid;
   c. contacting said uncoated, suspended smaller sized particles with said coating material, before substantial aggregation of said smaller sized particle occurs, for a time sufficient for said coating material to adhere to said substrate, thereby forming said resuspendable, coated magnetic particles.
   d. recovering said resuspendable, coated magnetic particle.

20. A process according to claim 1, wherein said uncoated, suspended particulate magnetic substrate is contacted with said coating material in an amount no greater than that which is sufficient to provide complete coverage of said resuspendable, coated magnetic particles.

21. A process according to claim 20, wherein a secondary coating material is applied to said coated particles.

22. A process according to claim 21, wherein said secondary coating material is a dispersion aid.

* * * * *